United States Patent [19]

Michalczyk et al.

[11] 3,969,371

[45] July 13, 1976

[54] PROCESS FOR CONVERTING γ-BUTYROLACTONE INTO TETRAHYDROFURAN

[75] Inventors: Georg Michalczyk, Neukirchen-Vluyn; Karl-Heinz Gluzek, Alpen, both of Germany

[73] Assignee: Deutsche Texaco Aktiengesellschaft, Hamburg, Germany

[22] Filed: July 15, 1974

[21] Appl. No.: 488,351

[30] Foreign Application Priority Data

Aug. 3, 1973 Germany............................ 2339344

[52] U.S. Cl............................ 260/346.1 R; 252/465
[51] Int. Cl.$^2$........................................ C07D 307/08
[58] Field of Search................. 260/346.1; 252/470, 252/465

[56] References Cited

UNITED STATES PATENTS 3,370,067    2/1968    Johnson........................... 260/346.1

FOREIGN PATENTS OR APPLICATIONS 4,740,770    10/1972    Japan............................... 260/346.1
1,293,151    10/1972    United Kingdom.............. 260/346.1

*Primary Examiner*—Harry I. Moatz
*Attorney, Agent, or Firm*—T. H. Whaley; C. G. Ries; George J. Darsa

[57] ABSTRACT

A process for converting γ-butyrolactone to tetrahydrofuran by treating the lactone with hydrogen in the presence of a cobalt-copper chromite catalyst at elevated pressures and temperatures.

4 Claims, No Drawings

PROCESS FOR CONVERTING γ-BUTYROLACTONE INTO TETRAHYDROFURAN

BACKGROUND OF THE INVENTION

The invention relates to a process for converting γ-butyrolactone into tetrahydrofuran by treating the lactone with hydrogen in the presence of a cobalt-copper chromite catalyst.

Various methods are known for the preparation of tetrahydrofuran as, for example, dehydrating tetramethyleneglycol or hydrogenating furan. More recent methods involve hydrotreating a dicarboxylic acid or a dicarboxylic acid anhydride and converting to tetrahydrofuran via the intermediate γ-butyrolactone. Likewise, γ-butyrolactone can itself be used as the starting material. For example, in U.S. Pat. No. 3,370,067 tetrahydrofuran is produced by the hydrogenolysis of butyrolactone in the presence of a supported platinum metal catalyst or a transition metal catalyst where the metal has an atomic number from 21 to 30. However, the results obtained employing these catalytic materials were unsatisfactory in that high conversions and high selectivity were not simultaneously achieved.

It is an object of this invention to provide a process for converting γ-butyrolactone to tetrahydrofuran in high yields.

Another object of this invention is to provide a selective process for converting γ-butyrolactone to tetrahydrofuran.

Yet another object of this invention is to provide a new catalyst for converting γ-butyrolactone to tetrahydrofuran.

Other objects and advantages will become apparent from a reading of the following detailed description and examples.

DESCRIPTION OF THE INVENTION

Broadly, this invention contemplates a process for converting γ-butyrolactone to tetrahydrofuran by treating the lactone with hydrogen in the presence of a cobalt-modified copper chromite catalyst. Generally, the process is conducted under elevated pressures and elevated temperatures. In one embodiment, conversion of γ-butyrolactone is undertaken in the presence of a cobalt-modified copper chromite catalyst under conversion temperatures ranging from about 100° to 350°C., preferably from about 250° to 300°C., and under pressures suitably in the range of from about 100 to 400 kg/cm², preferaby 150 to 200 kg/cm².

The novel cobalt-modified copper chromite catalyst employed in the aforementioned process comprises CoO, CuO, $Cr_2O_3$ and aluminum oxide. In general, the catalyst comprises from about 5.0 to 25.0, preferably 12.0 to 14.5, weight percent CoO, from about 5.0 to 30.0, preferably 12.5 to 16.0 weight percent CuO, from about 10.0 to 35.0, preferably 15.5 to 19.5 weight percent $Cr_2O_3$ and the balance aluminum oxide, for example eta or gamma alumina. The catalyst is employed in the process in amounts ranging from about 1:100 to 1:1 parts by weight of catalyst per weight of γ-butyrolactone. A highly satisfactory weight ratio is 0.5 to 1.5, particularly 1 part, by weight of the catalyst per 5 parts by weight of γ-butyrolactone. In a preferred embodiment of the invention, the reaction is carried out within three hours, at a temperature of 300°C. and under a pressure of 150 kg/cm².

The cobalt-modified copper chromite catalyst of the invention is prepared by adding to aluminum hydroxide a salt of cobalt and of copper, eg. nitrate, chloride or an organic salt, such as the acetate, and $CrO_3$ in an aqueous medium. After mixing and kneading the materials, the recovered mass is dried. The catalyst, after being ground and sieved is calcined for about 1 to 5 hours at from about 250 to 500°C., suitably at 450°C. in an inert gaseous environment such as argon, neon, helium and preferably in a stream of nitrogen. Subsequently, the catalyst is activated in a reducing environment, preferably in a stream of hydrogen, for 1 to 10 hours at about 200° to 300°C., preferably at 200 to 250°C. The so prepared catalyst is not pyrophoric nor does it lose its activity upon exposure to air. Moreover, it has a long catalyst life and is easily regenerated by heating with air at a temperature of from 200° to 500°C. and reducing with hydrogen at 150° to 450°C.

It was unexpectedly found that the instant cobalt-modified catalyst proved to be superior in conversion and selectivity for the reduction of γ-butyrolactone to tetrahydrofuran inasmuch as nickel catalysts had previously been considered as equivalent reaction catalysts. It has now been found that employing the cobalt-modified copper chromite catalyst of our invention permits high conversion at high selectivities to tetrahydrofuran from γ-butyrolactone, whereas corresponding nickel-modified catalysts are substantially less selective and produce substantially more byproducts.

The process of our invention is operated in the liquid phase, which is a considerable advantage over operating in the gaseous phase as far as conversion and reactor dimensions are concerned. The starting material, γ-butyrolactone is a well known material that can be provided by any of the methods heretofore taught by the art. In general, we employ the starting material in undiluted condition in our process. However, reaction diluents such as gaseous diluents, e.g., nitrogen, argon or methane, or liquid diluents such as hydrocarbons e.g., octane or cyclohexane, can be employed. However, there is no advantage to the use of diluents. Following the reaction, tetrahydrofuran is recovered by conventional means.

The product of our process, namely tetrahydrofuran represents a valuable material, particularly as a solvent or as a medium in a plurality of reactions. It is also useful in the manufacture of polytetramethylene glycol which in turn is used in the manufacture of synthetic fibers.

In order to more fully illustrate the nature of our invention and the manner of practicing the same, the following examples are presented. In these examples, the best mode contemplated by us for carrying out our invention is set forth.

EXAMPLE I

A cobalt-copper chromite catalyst according to the invention was prepared as follows. Aluminum-tri-secondary butylate (232 grams) was hydrolyzed with demineralized water and the formed alcohol was stripped. The aluminum hydroxide paste which had been concentrated to a volume of 200 ml. was admixed with a solution of 38.9 grams of $Cu(NO_3)_2.3H_2O$ in 35 ml. of water, 20.7 grams of $CrO_3$ in 20 ml. of water, 46.1 grams of $Co(NO_3)_2.6H_2O$ in 50 ml. of water and the mass was kneaded for 1 hour. The paste like product was dried at 110° to 120°C. for 1 day, thereafter ground, sieved and calcined for 3 hours at 450°C., in a stream of nitrogen. After cooling to 200°C. the stream of hydrogen was introduced at a flow rate of 33 liters per hour and the temperature raised to 250°C. within 1 hour. The activation was completed after 2 hours of hydrogen treatment. The so produced catalyst was not pyrophoric nor did it lose its activity upon exposure to air. The catalyst had the following composition in weight percent: 14.6 — CuO, 17.9 — $Cr_2O_3$, 13.5 — CuO and 54.0 — $Al_2O_3$.

Tetrahydrofuran was prepared from γ-butyrolactone as follows: A 2-liter autoclave equipped with stirring means was charged with 250 grams of γ-butyrolactone and 50 grams of the above-mentioned catalyst and the charge was hydrogenated at 150 kg/cm² for 4 hours at about 300°C. The composition of the product was determined by gas chromatography and the results are set forth in the Table below.

EXAMPLE II

A nickel-copper chromite catalyst was prepared according to the procedure of Example I except that a solution of 47.2 grams of $Ni(NO_3)_2.6H_2O$ in 50 ml. of water was employed in place of the cobalt nitrate solution. The catalyst had the following composition in weight percent: 14.6 — CuO, 17.9 — $Cr_2O_3$, 13.5 — NiO and 54.0 — $Al_2O_3$.

Tetrahydrofuran was prepared from γ-butyrolactone according to the procedure of Example I except that the nickel-copper chromite catalyst prepared above was employed. The composition of the product obtained was determined by gas chromatography and the results are set forth in the Table below.

EXAMPLE III

Another cobalt-copper chromite catalyst according to this invention was prepared as follows. An aluminum hydroxide paste was prepared from 249.5 grams of aluminum-trisecondary butylate as in Example I and mixed with solutions of 20.7 grams of $CrO_3$ in 20 ml. of water, 24.9 grams of $Cu(NO_3)_2.3H_2O$ in 25 ml. of water and 46.1 grams of $Co(NO_3)_2.6H_2O$ in 40 ml. of water and the mass was kneaded for one hour. As described in Example I, the mass was dried, calcined and activated. The catalyst had the following composition in weight percent: 13.9 — CuO, 17.0 — $Cr_2O_3$, 13.1 — CoO and 56.0 — $Al_2O_3$.

Hydrotreatment of γ-butyrolactone was undertaken in the presence of the catalyst prepared above according to the procedure of Example I except that hydrogenation was conducted for three hours at a pressure of 200 kg/cm². The composition of the product was determined by gas chromatography and the results are summarized in the Table below.

EXAMPLE IV

A nickel-copper chromite catalyst was prepared according to the following procedure. An aluminum oxide paste obtained from 235.5 grams of aluminum-tri-secondary butylate was mixed with the solutions of 44.7 grams of $Cu(NO_3)_2.3H_2O$ in 45 ml. of water, 27.6 grams of $CrO_3$ in 25 ml. of water and 61.5 grams of $Ni(NO_3)_2.6H_2O$ in 65 ml. of water and the mass was kneaded, dried, calcined and activated as described in Example I. The composition of the catalyst as weight percent was as follows: 14.6 — CuO, 21.0 — $Cr_2O_3$, 15.8 — NiO and 48.6 — $Al_2O_3$.

Hydrotreatment of γ-butyrolactone was undertaken in the presence of the catalyst prepared above in accordance with the procedure of Example III. The composition of the product was determined by gas chromatography and the results are summarized in the Table below.

EXAMPLE V

Another cobalt-copper chromite catalyst was prepared according to the procedure of Example I except that activation with hydrogen was undertaken for 2 hours at 200°C.

Tetrahydrofuran as prepared from γ-butyrolactone in the presence of the catalyst prepared above. The procedure of Example I was followed except that the charge was hydrogenated for 4.5 hours at a pressure of 200 kg/cm². The results are summarized in the Table below.

TABLE

| Example | THF | NPA | NBA | PSE | BSE | GBL | Other | Conversion mole-% | Selectivity |
|---|---|---|---|---|---|---|---|---|---|
| I | 86.9 | 1.3 | 5.1 | — | — | 0.6 | 6.9 | 99.4 | 87.5 |
| II | 66.5 | 7.7 | 5.0 | — | — | 6.7 | 14.1 | 93.3 | 71.2 |
| III | 85.9 | 0.6 | 3.2 | — | 0.6 | 3.6 | 6.0 | 96.4 | 89.2 |
| IV | 65.6 | 6.3 | 3.2 | 1.8 | 1.2 | 15.9 | 6.1 | 84.1 | 78.0 |
| V | 89.7 | 0.9 | 5.9 | 0.4 | 0.2 | 1.3 | 1.7 | 98.7 | 90.8 |

Meaning of abbreviations
THF   Tetrahydrofuran
NPA   n-Propanol
NBA   n-Butanol
PSE   Propionic Acid
BSE   Butyric Acid
GBL   γ-Butyrolactone
(Other) Ester, Butandiol-1,4

The foregoing examples show clearly the superior effectiveness of the cobalt-modified copper chromite catalyst of our invention.

In the examples, the hydrotreatment was carried out at temperatures in the range of from 290° to 300°C. Substantially higher temperatures, that is above 350°C. should be avoided. While pressures preferably in the range of between 150 and 200 kg/cm² are employed, higher or lower pressures can be used without substantially influencing the results. Depending on pressure, amount of catalyst charged and reactor volume, the reaction is completed within three to six hours. The catalyst addition may be varied within wide limits. Preferably, catalyst is added in an amount of 1 part by weight per 5 parts by weight of γ-butyrolactone. It is also possible to use 0.5 part by weight of catalyst, however, the hydrotreating period must then be correspondingly extended. Higher amounts of catalyst do not have any adverse effects, but are uneconomical.

We claim:

1. A process for converting γ-butyrolactone to tetrahydrofuran in the liquid phase which comprises treating said lactone with hydrogen in the presence of a cobalt modified copper chromite and aluminum oxide catalyst wherein said catalyst comprises from about 5.0 to 25.0 weight percent CoO, from about 5.0 to 30.0 weight percent CuO, from about 10.0 to 35.0 weight percent $Cr_2O_3$ and the balance aluminum oxide at a temperature of from about 100° to 350°C. and a pressure of from about 100 to 400 kg/cm².

2. A process according to claim 1 wherein said treating is conducted at a temperature of from about 250° to 300°C. and a pressure of from about 150 to 200 kg/cm².

3. A process according to claim 1 wherein from 0.5 to 1.5 parts by weight of said catalyst are employed per 5 parts by weight of γ-butyrolactone.

4. A process according to claim 1 wherein said catalyst comprises from about 12.0 to 14.5 weight percent CoO, from about 12.5 to 16.0 weight percent CuO, from about 15.5 to 19.5 weight percent $Cr_2O_3$ and the balance aluminum oxide.

* * * * *